US010043088B2

(12) United States Patent
Odry et al.

(10) Patent No.: US 10,043,088 B2
(45) Date of Patent: Aug. 7, 2018

(54) IMAGE QUALITY SCORE USING A DEEP GENERATIVE MACHINE-LEARNING MODEL

(71) Applicant: Siemens Healthcare GmbH, Erlangen (DE)

(72) Inventors: Benjamin L. Odry, West New York, NJ (US); Boris Mailhe, Plainsboro, NJ (US); Hasan Ertan Cetingul, Fulton, MD (US); Xiao Chen, Princeton, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/606,069

(22) Filed: May 26, 2017

(65) Prior Publication Data

US 2017/0372155 A1  Dec. 28, 2017

Related U.S. Application Data

(60) Provisional application No. 62/353,737, filed on Jun. 23, 2016.

(51) Int. Cl.
*G06K 9/03* (2006.01)
*G06K 9/62* (2006.01)
*G06K 9/66* (2006.01)

(52) U.S. Cl.
CPC ............... *G06K 9/03* (2013.01); *G06K 9/627* (2013.01); *G06K 9/6255* (2013.01); *G06K 9/6274* (2013.01); *G06K 9/6277* (2013.01); *G06K 9/66* (2013.01); *G06K 2209/05* (2013.01)

(58) Field of Classification Search
CPC .................................. G06K 9/00; G06K 9/03
See application file for complete search history.

(56) References Cited

U.S. PATENT DOCUMENTS

| 6,819,790 | B2 * | 11/2004 | Suzuki | G06T 7/0012 382/130 |
| 7,352,880 | B2 * | 4/2008 | Kim | G06K 9/00228 382/103 |
| 7,813,581 | B1 * | 10/2010 | Fitzpatrick | H04N 5/357 348/169 |
| 7,860,344 | B1 * | 12/2010 | Fitzpatrick | G06K 9/3241 345/419 |
| 8,861,884 | B1 * | 10/2014 | Fang | G06T 5/003 382/255 |

(Continued)

OTHER PUBLICATIONS

Bosse, Sebastian, et al. "A deep neural network for image quality assessment." Image Processing (ICIP), 2016 IEEE International Conference on. IEEE, 2016.

(Continued)

*Primary Examiner* — Anand Bhatnagar

(57) ABSTRACT

For image quality scoring of an image from a medical scanner, a generative model of an expected good quality image may be created using deep machine-learning. The deviation of an input image from the generative model is used as an input feature vector for a discriminative model. The discriminative model may also operate on another input feature vector derived from the input image. Based on these input feature vectors, the discriminative model outputs an image quality score.

20 Claims, 3 Drawing Sheets

(56) References Cited

U.S. PATENT DOCUMENTS

| | | | | |
|---|---|---|---|---|
| 8,866,936 B2* | 10/2014 | Barbu | ................ | G06K 9/40 |
| | | | | 348/241 |
| 8,942,477 B2* | 1/2015 | Tamura | ............ | H04N 1/409 |
| | | | | 382/169 |
| 9,965,719 B2* | 5/2018 | Choi | ................ | G06N 3/08 |
| 2004/0017930 A1* | 1/2004 | Kim | ............ | G06K 9/00228 |
| | | | | 382/103 |
| 2005/0010106 A1* | 1/2005 | Lang | ................ | A61B 6/469 |
| | | | | 600/425 |
| 2010/0020208 A1* | 1/2010 | Barbu | ................ | G06K 9/40 |
| | | | | 348/250 |
| 2016/0350620 A1* | 12/2016 | Rao | ................ | G06K 9/6256 |
| 2018/0012107 A1* | 1/2018 | Xu | ................ | G06K 9/6267 |

OTHER PUBLICATIONS

Hou, Weilong, et al. "Blind image quality assessment via deep learning." IEEE transactions on neural networks and learning systems 26.6 (2015): 1275-1286.

\* cited by examiner

IMAGE QUALITY SCORE USING A DEEP GENERATIVE MACHINE-LEARNING MODEL

RELATED APPLICATIONS

The present patent document claims the benefit of the filing date under 35 U.S.C. § 119(e) of Provisional U.S. Patent Application Ser. No. 62/353,737, filed Jun. 23, 2016, which is hereby incorporated by reference.

BACKGROUND

The present embodiments relate to scoring for image quality. In medical imaging, the process of image acquisition and reconstruction inevitably introduces artifacts. One or more of different types of artifacts, such as motion blur, noise, streaking artifacts, or intensity inhomogeneity, are in the generated image.

A scoring system assesses image quality after acquisition and helps determine whether enough significant clinical value may be extracted and therefore lead to correct diagnosis. The scoring system evaluates the extent and severity of artifacts by assigning the types of artifacts an integer number between 1 and 5. Global quality score is derived from those artifact specific scores. This process may be manual, so may be inconsistent. Computerized scoring schemes for photographs may not be applicable to medical images.

SUMMARY

By way of introduction, the preferred embodiments described below include methods, systems, instructions, and non-transitory computer readable media for image quality scoring of an image from a medical scanner. Using deep machine-learning, a generative model of an expected good quality image may be created. The deviation of an input image from the generative model is used as an input feature vector for a discriminative model. The discriminative model may also operate on another input feature vector derived from the input image. Based on these input feature vectors, the discriminative model outputs an image quality score.

In a first aspect, a method is provided for image quality scoring of an image from a medical scanner. The medical scanner generates the image representing a patient. The image has a level of artifacts due to the generating by the medical scanner. A machine determines a probability map of artifacts as a function of location for the image with a deep generative machine-learnt model and assigns a quality score for the image with application of the probability map to a discriminative machine-learnt classifier. The quality score for the image of the patient is transmitted.

In a second aspect, a method is provided for training a machine to determine an image quality score. The machine trains a deep generative model using a piecewise-differentiable function. The deep generative model is trained to output a spatial distribution of probability in response to an input image. The machine trains a discriminative classifier to output a score of image quality as a function of input of the spatial distribution of probability.

In a third aspect, a method is provided for image quality scoring of an image from a medical scanner. The medical scanner generates the image representing a patient. The image has a level of artifacts due to the generating by the medical scanner. A machine determines a probability map of artifacts as a function of location for the image with a deep generative machine-learnt model and assigns a quality score for the image with application of the probability map to a discriminative machine-learnt classifier. The probability map is a first input vector, and features of the image are a second input vector. The quality score for the image of the patient is transmitted.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A deep generative model is used for image quality scoring of medical or other images. Deep generative models directly evaluate the probability of a new image to belong to the same category as the training data. For example, deep generative models may learn from multiple images of birds how to generate an image of a bird. While those models have shown their ability to synthesize natural-looking images, such as of a bird, the generative models have seen little use in other tasks due to their complexity, which does not allow easy manipulation by an inference or optimization algorithm. The use of deep generative models in medical imaging is sparse.

Scoring of image quality is based on the presence of any artifacts in the image, as well as the extent and/or severity of the artifacts. Often, both criteria are scored independently and manually, and a global assessment score is consequently derived. Rather than manual scoring, discriminative and generative features are combined to produce a score. An image quality score is based on learnt deep image features, including features output by a generative model.

Figure 1:
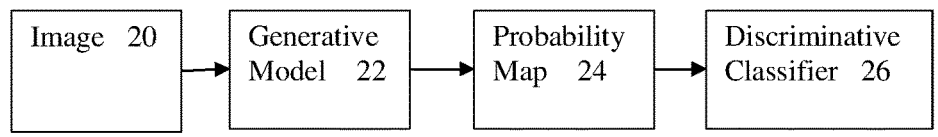
FIG. 1 illustrates an example process chain using a generative model for scoring an image for quality.

FIG. 1 illustrates one embodiment of a process flow or chain. The process represents machine training or application of machine-learnt models. Two or more instances of machine training or application are performed. A generative model 22 is learned. The generative model 22 learns to output a probability map 24 based on input of an image 20 to be scored. A discriminative classifier 26 learns to use the output of the generative model 22 (i.e., the probability map 24) to score. The generative model 22 may be learned as part of learning the discriminative classifier 26, or the two are separately machine-learnt.

Figure 2:
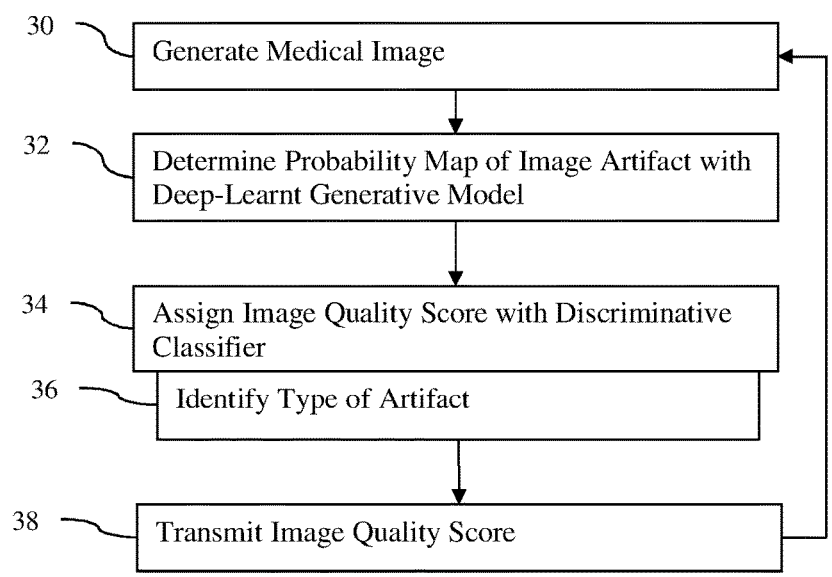
FIG. 2 illustrates one embodiment of a method for image quality scoring of an image from a medical scanner.

FIG. 2 shows one embodiment of a method for image quality scoring of an image from a medical scanner. FIG. 2 is directed to application of the generative model 22 and the discriminative classifier 26. The method is illustrated in the context of medical imaging, but may be applied in other contexts (e.g., photographs, material testing, astronomy, or seismic sensing). The generative model 22 determines the probability map 24 of spatial distribution of likelihood of normality of the input image 20. The discriminative classifier 26 uses the probability map 24 to assign a score of the quality of the input image 20.

Additional, different, or fewer acts may be provided. For example, act 30 is replaced with loading a medical image or other type of image. As another example, acts 36 and/or 38 are not performed.

Figure 5:
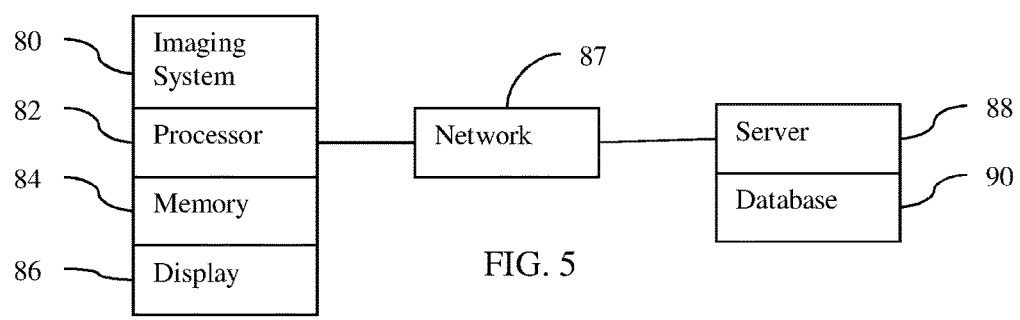
FIG. 5 is a block diagram of one embodiment of a system for machine learning and/or for use of machine-learnt models for image quality scoring.

The acts are performed by the system of FIG. 5, other systems, a medical scanner, a workstation, a computer, and/or a server. For example, 30 is performed by a medical scanner. Acts 32-38 are performed by a processing component, such as the medical scanner, a workstation, or a computer. The acts are performed in the order shown (e.g., top to bottom) or other orders.

In act 30, a medical scanner generates an image representing a patient. The image is made available by or within the medical scanner. A processor may extract the data from a picture archive communications system or a medical records database. Alternatively, data not in the medical environment is acquired, such as capturing or loading a photograph or video. Other sensors may generate an image in alternative embodiments, such as a camera.

The medical image or dataset is acquired by the medical scanner. Alternatively, the acquisition is from storage or memory, such as acquiring a previously created dataset from a PACS. Acquisition may be through transmission over a network.

The image is medical imaging data. The medical image is a frame of data representing the patient. The data may be in any format. While the terms image and imaging are used, the image or imaging data may be in a format prior to actual display of the image. For example, the medical image may be a plurality of scalar values representing different locations in a Cartesian or polar coordinate format different than a display format. As another example, the medical image may be a plurality red, green, blue (e.g., RGB) values output to a display for generating the image in the display format. The medical image may be currently or previously displayed image in the display or another format. The image or imaging is a dataset that may be used for imaging, such as scan data representing the patient.

Any type of medical image and corresponding medical scanner may be used. In one embodiment, the medical image is a computed tomography (CT) image acquired with a CT system. For example, a chest CT dataset may be used for detecting a bronchial tree, fissures, and/or vessels in the lung. For CT, the raw data from the detector is reconstructed into a three-dimensional representation. As another example, magnetic resonance (MR) data representing a patient is acquired. MR data is acquired with an MR system. The data is acquired using a pulse sequence for scanning a patient. Data representing an interior region of a patient is acquired. For MR, the magnetic resonance data is k-space data. Fourier analysis is performed to reconstruct the data from the k-space into a three-dimensional object or image space. The data may be ultrasound data. Beamformers and a transducer array scan a patient acoustically. The polar coordinate data is detected and processed into ultrasound data representing the patient. The data may be positron emission tomography (PET), single photon emission computed tomography (SPECT), or other nuclear imaging data. Radioactive emissions from within the patient are detected and reconstructed into imaging data.

The medical image represents tissue and/or bone structure of the patient. Alternatively, the medical image represents flow, velocity, or fluids within the patient. In other embodiments, the medical image represents both flow and structure. For PET and SPECT, the scan data represents function of the tissue, such as uptake.

The medical image represents a one, two, or three-dimensional region of the patient. For example, the medical image represents an area or slice of the patient as pixel values. A three-dimensional volume may be represented as pixel values by rendering to a two-dimensional format. As another example, the medical image represents a volume or three-dimensional distribution of voxels. Values are provided for each of multiple locations distributed in two or three dimensions. The medical image is acquired as a frame of data. The frame of data represents the scan region at a given time or period. The dataset may represent the area or volume over time, such as providing a 4D representation of the patient.

The image may include one or more artifacts. Different modalities of imaging are susceptible to different types of artifacts. The physics for scanning and/or the processing to create the image from the scan may generate an artifact. Motion of the patient or sensor performing the scan may generate an artifact. Example artifacts in medical imaging include noise, blur (e.g., motion artifact), shading (e.g., blockage or interference with sensing), and/or under-sampling artifacts.

Any level of artifact may exist. The scan settings for the medical scanner, condition of the patient, amount of movement, filtering, reconstruction, other image processing, and/or other factors may contribute to different levels of artifacts in an image. One image may include one type or multiple types of artifacts. The level may be a function of the severity (e.g., intensity or contrast) and/or extent (e.g., distribution or number of instances).

The scoring is based on specific artifacts and/or artifacts in general. The level of artifact in any given image is to be detected.

In act 32, a machine determines a probability map of artifacts as a function of location for the image with a deep generative machine-learnt model. Any machine capable of applying the deep generative machine-learnt model may be used. For example, a computer inputs the image to learned matrices or a matrix learned as the deep generative machine-learnt model.

Any machine-learnt generative model may be used. The generative model encodes the data to a few independent latent variables, and generates synthetic data by sampling the latent variables. In deep learning, the latent variables are learned by the machine training. For the generative model for image quality scoring, the model only takes an image as input, but other inputs may be provided, such as clinical data of a patient. The generative model returns a prior log-likelihood and is implemented as a piecewise-differentiable function such as used in deep learning. For example, the generative model is a deep learnt model using restricted Boltzmann machines, deep belief network, neural autoregressive density estimators, variational auto-encoders, extensions thereof, or other deep learning approaches for generative modeling. In one embodiment, the trained deep generative model is a deep neural network with a set of j convolutional layers and k fully connected layers, each followed by a non-linear activation function, and a set of pooling layers for features reduction. Other layer arrangements may be used.

Figure 3:
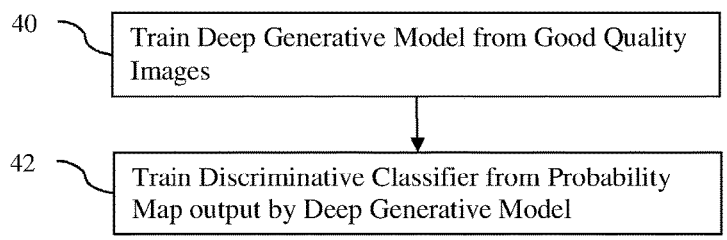
FIG. 3 is a flow chart diagram of one embodiment of a method for training a machine to determine an image quality score.

FIG. 3 shows one embodiment of a flow chart of a method for training a machine to determine an image quality score. The method is implemented by a computer, workstation, server, or other processing component with access to a database of hundreds or thousands of example images with known quality scores and/or types of artifacts. The acts are performed in the order shown with any amount of separation in time between act 40 and act 42. Additional or different acts may be provided.

In act 40, the machine learns the generative model from the images of the database. Using a piecewise-differentiable function or other deep learning function, the machine trains the deep generative model to output a spatial distribution of probability in response to an input image.

The images from the database used for training the deep generative model are of similar quality, such as a desired good quality. The level of artifact or quality score is above or below a threshold level, depending on whether higher or lower scores indicate better quality. All the images used for training the generative model are of good or the top image quality. Any threshold for quality may be used for the training images, such as only a score of 5 in a score range of 1-5 where 5 is the best quality. In alternative embodiments, a broader range (e.g., moderate level, low level, and/or no artifacts in the images) is used. In yet other embodiments, images of any quality level are used.

To train the generative model, the model is fed with a set of images of good or similar quality (e.g., determined by their score). The log-likelihood of the output is maximized. The generative model encodes features that represent the good qualities in the images. Since generative training is unsupervised, training does not require matched pairs of good and bad images, which is difficult to acquire on a large scale in a medical setting. To obtain both good and bad images requires scanning patients twice and results in extra dose and/or scan time for with no immediate benefit to the patient.

The generative nature is used to determine a model of a good quality image. This holistic data acquisition process results in a larger quantity of training data that discriminative approaches may train each network only on images featuring one particular kind of distortion. The generative model provides features or kernels used to indicate a good quality image, which features may be used for discriminative detection of any number of types of artifacts.

The generative model is trained with deep machine learning to output a probability of an input image matching good qualities. Returning to act 32 of FIG. 2, the probability map for an input image is determined. The probability map is a spatial distribution of probability of normality or abnormality. Abnormality reflects the likelihood of an artifact. The map is a spatial distribution, such as calculating the probability for each pixel or voxel based on the intensities or values of surrounding or neighboring pixels or voxels.

The model parameters (e.g., machine trained features, kernels or layer values) are used to compute the probability for each voxel that its intensity fits the generative model of good quality. Voxels or pixels with intensity and neighborhood intensity distribution that do not match those of the generative model will have a low probability, hence creating a map of potential abnormalities. Voxels or pixels with intensity and neighborhood intensity distribution that do match those of the generative model will have a high probability, hence creating a map of potential normalities. Inverse probabilities may be used. The map is a spatial distribution of probability of normalcy and/or abnormality. Matching to a generative model of poor or low quality images may be used in other embodiments.

The probability map is determined as a function of log-likelihoods of the locations of the image matching the deep generative machine-learnt model. The deep learnt generative model encoding provides a log-likelihood of the input, represented as:

$$L(X) = \frac{1}{2\sigma^2}\|Y - A_n X\|^2 - \log p(X)$$

where L is the loss that drives the training of the model, a is STD of the input distribution, Y is true target image, $A_n$ is the set of parameters for the model, X is the input image, and $-\log p(X)$ is the output of the generative model. For each voxel or pixel, a corresponding probability, p(X), is computed with the generative model. Other resolutions for the probability map, such as less spatial resolution that the voxels or pixels may be used.

The probabilities may be used as the probability map input to the discriminative classifier. Alternatively, the probability map is formulated as a deviation of the input image from the probabilities. For example, the probability map is calculated as: deviation of p(x)=1−p(X), emphasizing the deviation from the model of a normal image.

In act 34, the machine assigns a quality score for the image. The probability map is applied to a discriminative machine-learnt classifier. Other inputs may be used, such as clinical data for the patient and/or features extracted from the image other than the probability map.

The score to be assigned is a global score or score for artifacts in general. Alternatively or additionally, separate scores are to be provided for different types of artifacts (e.g., separate blur and noise scores). The severity and extent of the artifacts may be separately scored or one score encompassing artifact level that is a function of both severity and extent is used.

In one embodiment, the score, S, is represented as $S=(s_1, \ldots, s_n)$ with $s_i=(sev, ext)$ for severity and extent of artifact i (out of n artifact types). This provides a global score that is a function of scores for each type of artifact.

The discriminative machine-learnt classifier is any type of machine-learnt classifier that receives input features (e.g., feature values derived from the probability map) and outputs a classification (e.g., score). Support vector machine, Bayesian network, a probabilistic boosting tree, neural network, sparse auto-encoding classifier, or other now known or later developed machine learning may be used. Any semi-supervised, supervised, or unsupervised learning may be used. Hierarchal, cascade, or other approaches may be used.

In one embodiment, a neural network (e.g., deep neural network) is used. Other deep learnt, sparse auto-encoding classifiers may be trained and applied. The machine training is unsupervised in learning the features to use and how to classify given the learnt feature vector. A function $\varphi(X, \theta)$ is trained, where X is the probability map and $\theta$ the model parameter (i.e., network parameters) such that the predicted score $S^*=\varphi(X, \theta)$.

Referring to FIG. 3, the machine trains the discriminative classifier in act 42. For example, a deep neural network is trained to estimate φ with a $L_2$ loss (e.g., least squares error) or other loss to obtain optimal network parameters. The training may be represented by:

$$\underset{(X,S)}{\mathrm{argmin}} \sum \sum_{i=1}^{n} \|s_i - \varphi_i(X, \theta)\|_2^2.$$

The difference between the ground truth or known scores for the training images and the prediction by the discriminative classifier is minimized.

The discriminative classifier is trained with training data. Samples of input data with ground truth are used to learn to classify the score. For deep learning, the classifier learns the features of the input data to extract from the training data. Alternatively, the features, at least for the input, are manually programmed, such as filtering the scan data and inputting the results of the filtering. The training relates the input data to the classification through one or more layers. One layer may relate feature values to the class. For deep-learnt networks, there may be further layers creating further abstract features from outputs of pervious layers. The resulting machine-trained classifier is a matrix for inputs, weighting, and combination to output a classification and/or probability of class membership. The deep machine-trained classifier includes two or more layers relating the input to the class.

The discriminative classifier is trained to output a score of image quality. Any scoring may be used. For example, a numerical range representing quality is provided, such as 1-5 or 1-10, where the larger or smaller number represents highest quality. As another example, alphanumeric classes are used, such as poor or good or such as poor, below average, average, good, or excellent.

The discriminative classifier is trained to assign the class based on the input features from the spatial distribution of probability. For example, deep learning is performed. The input is the deviation of the input image from the deep generative model. The discriminative classifier learns features to extract from this probability map and learns to relate values of the features to the class (i.e., score). The learnt features from the deep learning are a (k,n) matrix for predicted scoring. In additional or alternative embodiments, manually programmed features (e.g., Haar wavelets, steerable features, maximum detection) are extracted from the probability map as the matrix of the input feature vector.

Other input features may be used in addition to features derived from the probability map. For example, clinical data (e.g., family history, symptoms, test results, and/or diagnosis) is input or features derived therefrom are input. In one embodiment, features derived directly from the input image are used. In addition to the probability map, features of the intensities in the image are calculated. The features are learned as part of deep learning and/or are manually programmed features. The training uses input of both the spatial distribution of probability and deep learnt or other features extracted from the input image.

After creation, the machine-learnt discriminative classifier includes one or more layers. For a manually programmed features, one layer is a network relating the features of the input vector or input vectors (e.g., (k,n) matrix) to the class. For a deep-learnt network, at least one feature layer is learned from the training data rather than manually programmed. More than two layers may be provided, such as a neural network with three or more layers.

In one embodiment, a deep regressor is trained to estimate image quality score based on at least the probability distributions. These probability-based features from the generative model may be combined or concatenated with features computed from an associated discriminative model, such as deep learnt features from the input image other than the probability map.

Figure 4:
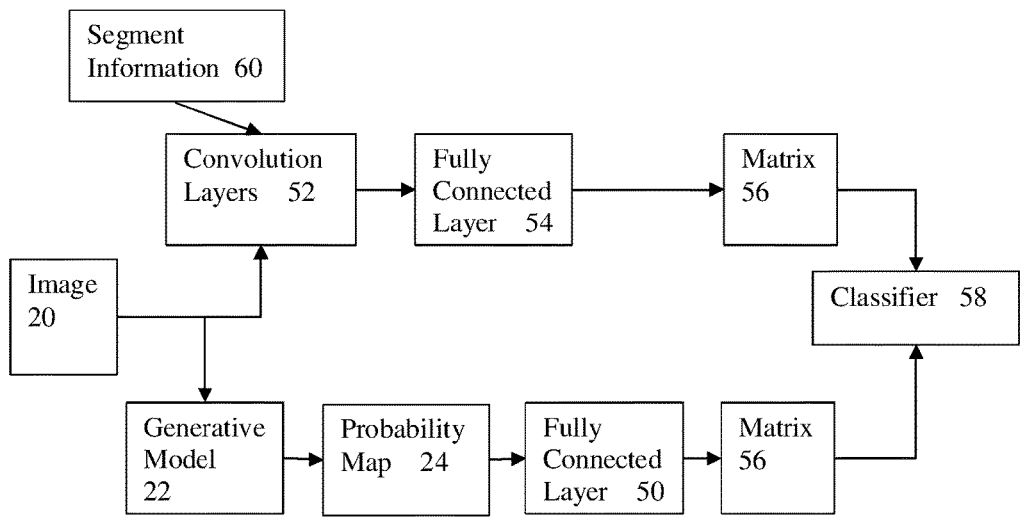
FIG. 4 illustrates another example process chain using a generative model for scoring an image for quality.

FIG. 4 shows one embodiment of a machine-learnt discriminator classifier process chain. The discriminator classifier is a deep learnt neural network. Like FIG. 1, the image 20 is input to the machine-learnt generative model 22, which results in a probability map 24 of the likelihood of abnormality or deviation from the generative model. This probability map 24 is further encoded for feature reduction in the fully connected layer 50. A convolution layer may be used instead of the fully connected layer 50. Additional layers may be provided. The output of the fully connected layer 50 is an input feature vector 56 of values derived from the probability map 24.

The image 20 is also input to a series of convolution layers 52, which output to the fully connected layer 54. Additional, different, or fewer layers 52, 54 may be provided. The layers 52, 54 are trained using deep learning to extract features from the image 20. The output of the fully connected layer 50 is an input feature vector 56 of values derived from the image 20 instead of the probability map. Other paths for creating input feature vectors may be used.

The classifier 58 assigns the image quality score with the application of the probability map and application of the image to the discriminative machine-learnt classifier. One set of features 56 used by the discriminative machine-learnt classifier is derived from the probability map 24 and another set of features 56 used by the discriminative machine-learnt classifier is derived from the image 20 without using the generative model. One input vector is learned from training images, and another input vector is learned from training probability maps.

Referring again to FIG. 2, the machine assigns the quality score in act 34. By application of the input feature vector or vectors, the discriminative classifier relates the values of the features to the score. The score classes are based on the training. Where the scores used for training include consideration of severity and extent of the artifacts, the score output by the classifier provides an indication of the severity and extent of the artifacts in the input image for a particular patient and/or scan.

In addition to outputting the score, the classifier may output additional information. A probability of class membership may be output (e.g., 75% likelihood of being good quality and 25% likelihood of being poor quality).

In one embodiment, the discriminative classifier is trained as a multi-task classifier. A cascade or hierarchy of classifiers may be used instead of or as a multi-task classifier. Any other class may be used for the multi-classification. In one approach, the machine identifies a type of artifact or types of artifacts with the score in act 36. For example, the discriminative classifier assigns a score of 4 for an image and identifies a blur artifact. As another example, the discriminative classifier assigns a score of 3 and identifies blur and oversampling artifacts. Separate scores and corresponding types of artifacts may be output. The severity and/or extent may be indicated as a class. Multi-task training adds multiple losses to obtain network parameters for multiple classes.

The generative model and/or the discriminative classifier are trained and used for specific circumstances. Different generative models and/or discriminative classifiers are provided for different circumstances. For example, the model and/or classifier are specific to diagnosis, artifact, scan modality, tissue of interest, type of patient, or other environmental or clinical situation. In other embodiments, the generative model and/or discriminative classifier are trained for and applied over a range of situations. For example, the same generative model and classifier are used for any type of artifact in any tissue associated with a particular scan modality.

In act 38, the machine transmits the quality score for the image of the patient. The transmission is over a network, through a communications interface, into memory or database (e.g., to a computerized patient medical record), or to a display. For example, the image quality score is displayed with the image of the patient. The score is an annotation, part of a pop-up, or part of a notice.

In one embodiment, the image quality score ranges from 1 to 5, from best to worst. The score is based on the presence of specific artifacts. The extent and/or severity of artifacts throughout the image may be reflected in the score. Other information may be transmitted with the score, such as the type of artifacts or other outputs of a multi-task discriminative classifier.

Referring to FIG. 4, the discriminative machine-learnt classifier, the deep generative machine-learnt model, or both may be responsive to segmentation of the image. FIG. 4 shows segmentation information 60 input to the convolution layers 52 for deriving feature values from the image. Alternatively or additionally, the segmentation information 60 is input to the generative model 22 or fully connected layer 50 for deriving feature values based on the probability map 24. Any of the generative model, features, and/or discriminative classifier use the segmentation.

The segmentation information 60 is anatomical or other image information. The segmentation distinguishes between foreground and background or identifies anatomical locations (e.g., identifying anatomical symmetry). Any segmentation may be used, such as thresholding, boundary detection, or histogram analysis.

Anatomical information may be incorporated in the assessment as some artifacts might be better seen in the background or the foreground. Separate generative models, features, and/or discriminative classifiers may be applied to the foreground and background. The results may then be combined to provide a score for the image. Alternatively, separate results for foreground and background are output.

Anatomical symmetry or locations (e.g., patches) with known relationships (e.g., similar or dis-similar tissue) may be used for comparison. Separate classification, probability maps, or features may be used. The results may be compared. The comparison may be input as a feature. In the generative model, the training and application may use the comparison as the comparison may indicate what is normal or abnormal.

A coordinate system referenced to the anatomy may be used for the classification. An anatomy-based coordinate system may be defined to normalize localization in the image. This may allow for comparison. The normalization may scale or register (spatially transform) the training images and input image to a same scale or alignment. Alternatively, the images are scaled and/or aligned as a precursor to use in training or application. The anatomical-based coordinate may be paired to the region or patch being regressed so that the same anatomy is considered for each image.

Referring again to FIG. 2, the user or the medical scanner uses the image quality score. The time, effort, and/or exposure to radiation (e.g., x-rays) for a scan are to be avoided when possible. A sufficiently good quality image allows for diagnosis with lest risk for error. A poor-quality image may not be sufficient for diagnosis, so the patient is scanned again. The score is used to scan again only when needed. Once the global image quality score or artifact-specific score is predicted, the operator of the medical scanner or the medical scanner decides whether to rescan the patient (i.e., whether to repeat the generation of the medical image in act 30). The score is used for a decision to use or not use the generated image. The result is that a later physician review is more likely to have a useful image for diagnosis, and rescanning is avoided where possible.

FIG. 5 shows one embodiment of a system for use in machine learning and/or for application. The system is distributed between the imaging system 80 and a remote server 88. In other embodiments, the system is just the server 88 or just the imaging system 80 without the network 87. In yet other embodiments, the system is a computer or workstation.

The system includes an imaging system 80, a processor 82, a memory 84, a display 86, a communications network 87, a server 88, and a database 90. Additional, different, or fewer components may be provided. For example, network connections or interfaces are provided, such as for networking with a medical imaging network or data archival system. In another example, a user interface is provided. As another example, the server 88 and database 90 are not provided, or only the server 88 and database 90 are provided. In other examples, the server 88 connects through the network 87 with many imaging systems 80 and/or processors 82.

The processor 82, memory 84, and display 86 are part of the medical imaging system 80. Alternatively, the processor 82, memory 84, and display 86 are part of an archival and/or image processing system, such as associated with a medical records database workstation or server, separate from the imaging system 80. In other embodiments, the processor 82, memory 84, and display 86 are a personal computer, such as desktop or laptop, a workstation, a server, a network, or combinations thereof. The processor 82, display 86, and memory 84 may be provided without other components for acquiring data by scanning a patient.

The imaging system 80, processor 82, memory 84 and display 86 are provided at a same location. The location may be a same room, same building, or same facility. These devices are local relative to each other and are remote to the server 88. The server 88 is spaced apart by the network 87 by being in a different facility or by being in a different city, county, state, or country. The server 88 and database 90 are remote from the location of the processor 82 and/or imaging system 80.

The imaging system 80 is a medical diagnostic imaging system. Ultrasound, computed tomography (CT), x-ray, fluoroscopy, positron emission tomography (PET), single photon emission computed tomography (SPECT), and/or magnetic resonance (MR) systems may be used. The imaging system 80 may include a transmitter and includes a detector for scanning or receiving data representative of the interior of the patient.

In one embodiment, the imaging system 80 is a CT system. An x-ray source is connected with a gantry. A detector is also connected with a gantry opposite the x-ray source. The patient is positioned between the source and detector. The source and detector are on opposite sides of the patient and rotate and/or translate about the patient. The detected x-ray energy passing through the patient is converted, reconstructed or transformed into data representing different spatial locations within the patient.

In another embodiment, the imaging system 80 is a MR system. The MR system includes a main field magnet, such as a cryomagnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data. The received k-space data is converted into object or image space data with Fourier processing.

The memory 84 may be a graphics processing memory, a video random access memory, a random access memory, system memory, cache memory, hard drive, optical media, magnetic media, flash drive, buffer, database, combinations thereof, or other now known or later developed memory device for storing data or video information. The memory 84 is part of the imaging system 80, part of a computer associated with the processor 82, part of a database, part of another system, a picture archival memory, or a standalone device.

The memory 84 stores medical imaging data representing the patient, weights or values of parameters making up some of the layers of the machine-learnt classifier, outputs from different layers, one or more machine-learnt matrices, and/or images. The memory 84 may store data during processing for application and/or may store training data (e.g., images and scores).

The memory 84 or other memory is alternatively or additionally a non-transitory computer readable storage medium storing data representing instructions executable by the programmed processor 82 for training or use of a machine-learnt classifier in medical imaging. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 82 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for training or applying machine-learnt classification. The processor 82 is a single device or multiple devices operating in serial, parallel, or separately. The processor 82 may be a main processor of a computer, such as a laptop or desktop computer, or may be a processor for handling some tasks in a larger system, such as in the imaging system 80. The processor 82 is configured by instructions, design, hardware, and/or software to perform the acts discussed herein.

The processor 82 is configured to perform the acts discussed above for training or application. The processor 82 uses a stored matrix or stored matrices for the machine-learnt generative model. The probability map is created by application of the input image to the generative model. The processor 82 derives features from the probability map. Features may be derived from other sources, such as the input image. The processor 82 uses a stored matrix or matrices for the machine-learnt discriminative classifier. The score is output by application of the values of the features to the discriminative classifier.

The processor 82 is configured to transmit the score, with or without other classification, over the network 87, to the display 86, or to the memory 84. The processor 82 may be configured to generate a user interface for receiving corrections or verification of classification results.

The display 86 is a monitor, LCD, projector, plasma display, CRT, printer, or other now known or later developed devise for outputting visual information. The display 86 receives images, graphics, text, quantities, or other information from the processor 82, memory 84, imaging system 80, and/or server 88. One or more medical images are displayed. The images are of a region of the patient. The image includes an indication, such as a graphic or colorization, of the classification results, such as the global score, artifact specific scores, and/or types of artifacts. The artifacts may be localized or detected and highlighted, such as detection as another class output by the discriminative classifier. The score may be displayed as the image without a medical image representation of the patient.

The network 87 is a local area, wide area, enterprise, another network, or combinations thereof. In one embodiment, the network 87 is, at least in part, the Internet. Using TCP/IP communications, the network 87 provides for communication between the processor 82 and the server 88. Any format for communications may be used. In other embodiments, dedicated or direct communication is used.

The server 88 is a processor or group of processors. More than one server 88 may be provided. The server 88 is configured by hardware and/or software. In one embodiment, the server 88 performs machine learning with training data in the database 90. The machine-learnt matrices are provided to the processor 82 for application. The results of classification may be received from the processor 82 for use in further training. Alternatively, the server 88 performs the application on an image received from the imaging system 80 and provides the score to the imaging system 80.

The database 90 is a memory, such as a bank of memories, for storing training data, such as images and respective scores. Weights or values of parameters of the generative model and/or discriminative classifier are stored in the database 90 and/or the memory 84.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for image quality scoring of an image from a medical scanner, the method comprising:
    generating, by the medical scanner, the image representing a patient, the image having a level of artifacts due to the generating by the medical scanner;
    determining, by a machine, a probability map of artifacts as a function of location for the image with a deep generative machine-learnt model;
    assigning, by the machine, a quality score for the image with application of the probability map to a discriminative machine-learnt classifier; and
    transmitting the quality score for the image of the patient.

2. The method of claim 1 wherein generating comprises generating computed tomography, magnetic resonance, ultrasound, positron emission tomography, or single photon emission computed tomography image.

3. The method of claim 1 wherein generating comprises generating a two-dimensional representation of pixels or a three-dimensional set of voxels as the image.

4. The method of claim 1 wherein generating comprises generating with noise artifact, blur artifact, shading artifact, under-sampling artifact, or combinations thereof.

5. The method of claim 1 wherein determining comprises determining with the deep generative machine-learnt model learnt with only training images having a quality above a threshold.

6. The method of claim 1 wherein determining comprises determining the probability map as a function of log-likelihoods of the locations of the image matching the deep generative machine-learnt model.

7. The method of claim 1 wherein determining comprises determining the probability map as a deviation from the deep generative machine-learnt modeled normal image.

8. The method of claim 1 wherein assigning the quality score comprises assigning with the discriminative machine-learnt classifier comprising a deep neural network.

9. The method of claim 1 wherein assigning comprises assigning the quality score as a function of severity and extent of the artifacts.

10. The method of claim 1 further comprising identifying a type of the artifacts, the assigning and identifying being performed with the discriminative machine-learnt classifier being a multi-task classifier, and wherein transmitting comprises transmitting the quality score and the type of the artifacts.

11. The method of claim 1 wherein assigning comprises assigning with the application of the probability map and application of the image to the discriminative machine-learnt classifier, a first set of features used by the discriminative machine-learnt classifier derived from the probability map and a second set of features used by the discriminative machine-learnt classifier derived from the image.

12. The method of claim 1 wherein the discriminative machine-learnt classifier, the deep generative machine-learnt model, or both are responsive to segmentation of the image.

13. The method of claim 1 wherein transmitting comprises transmitting the quality score to a display with the image.

14. The method of claim 1 further comprising scanning the patient again with the medical scanner in response to the quality score.

15. A method for training a machine to determine an image quality score, the method comprising:
    training, by the machine, a deep generative model using a piecewise-differentiable function, the deep generative model trained to output a spatial distribution of probability in response to an input image; and
    training, by the machine, a discriminative classifier, the discriminative classifier trained to output a score of image quality as a function of input of the spatial distribution of probability.

16. The method of claim 15 wherein training the deep generative model comprises training using images as training data, all the images having a threshold level of the image quality, the output being a probability of matching.

17. The method of claim 15 wherein training the discriminative classifier comprises training with deep learning where the probability input is a deviation of the input image from the deep generative model.

18. The method of claim 15 wherein training the discriminative classifier comprises training with the input of the spatial distribution of probability and deep learnt features extracted from the input image.

19. A method for image quality scoring of an image from a medical scanner, the method comprising:
    generating, by the medical scanner, the image representing a patient, the image having a level of artifacts due to the generating by the medical scanner;
    determining, by a machine, a probability map of artifacts as a function of location for the image with a deep generative machine-learnt model;
    assigning, by the machine, a quality score for the image with application of the probability map to a discriminative machine-learnt classifier, the probability map comprising a first input vector and features of the image comprising a second input vector; and
    transmitting the quality score for the image of the patient.

20. The method of claim 19 wherein the discriminative machine-learnt classifier comprises a deep learnt classifier, the second input vector learned training images and the first input vector learned from training probability maps.

* * * * *